United States Patent [19]

Schneider et al.

[11] Patent Number: 5,652,640
[45] Date of Patent: *Jul. 29, 1997

[54] VISION SIMULATING APPARATUS AND METHOD

[76] Inventors: Richard T. Schneider, 17 Alachua Highlands, Alachua, Fla. 32615;
Richard H. Keates, 71 Whitman Court, Irvine, Calif. 92715

[*] Notice: The term of this patent shall not extend beyond the expiration date of Pat. No. 5,532,770.

[21] Appl. No.: 633,674

[22] Filed: Apr. 17, 1996

Related U.S. Application Data

[63] Continuation-in-part of Ser. No. 423,104, Apr. 18, 1995, Pat. No. 5,532,770.
[51] Int. Cl.⁶ .................. A61B 3/10; A61B 3/00
[52] U.S. Cl. .................................. 351/205; 351/246
[58] Field of Search .......................... 351/200, 205, 351/246; 623/6

[56] References Cited

U.S. PATENT DOCUMENTS

| | | | |
|---|---|---|---|
| 4,927,260 | 5/1990 | Gordon | 351/205 X |
| 5,192,318 | 3/1993 | Schneider et al. | 623/6 |
| 5,354,335 | 10/1994 | Lipshitz et al. | 623/6 |
| 5,532,770 | 7/1996 | Schneider et al. | 351/205 |

OTHER PUBLICATIONS

A *J Cataract Refract Surg* article entitled "Small-diameter corneal inlay in presbyopic or pseudophakic patients," vol. 21, pp. 519-521, dated Sep., 1995.

*Primary Examiner*—Huy Mai
*Attorney, Agent, or Firm*—Merchant, Gould, Smith, Edell, Welter & Schmidt P.A.

[57] ABSTRACT

The invention includes apparatus and methods for evaluating vision through an intraocular lens. An image passes through a cornea, an intraocular lens, and a fovea window that are in a collinear array. In addition, the apparatus can include a human eye model, a fovea projector, and readable targets. The apparatus can be used to evaluate the vision of a subject through an intraocular lens such as a monofocal or bifocal intraocular lens. The ability of the subject to focus on one or more images at the fovea window provides information for evaluation of the subject's ability to see through an intraocular lens. Through movement of the fovea window or the intraocular lens dimensions or geometric constants of the subject's eye can be determined. The apparatus can also be used to evaluate vision through a bifocal cornea.

30 Claims, 12 Drawing Sheets

VISION SIMULATING APPARATUS AND METHOD

RELATED APPLICATION

This application is a continuation-in-part of application Ser. No. 08/423,104, filed Apr. 18, 1995, now U.S. Pat. No. 5,532,770.

FIELD OF THE INVENTION

This invention relates generally to apparatus and methods for use in simulating vision through an eye and for use in testing implanted intraocular lenses and corneal inlays.

BACKGROUND OF THE INVENTION

Intraocular lenses (IOLs) are used as artificial lens implants in eyes from which the natural lens has been removed. A natural lens changes its focal length by deformation, known as accommodation, to provide a focused image. An IOL does not focus in this manner. Monofocal IOLs provide focused vision at only a single distance range. If the focal length is selected to provide a sharp image for a distant object, then an object which is closer, for example at reading distance, will not be sharply focused on the retina. It is possible to sharply image closer objects by selecting a different focal length, but then distant objects would appear out of focus.

Bifocal IOLs are advantageous for providing clear vision at two distance ranges. U.S. Pat. No. 5,192,318, issued Mar. 9, 1993, the disclosure of which is incorporated by reference, concerns various bifocal IOL constructions. A bifocal IOL produces two superimposed images with one image always out of focus. Not all people can select between the two images and process the focused image sufficiently to see. Prior to surgery to implant a bifocal IOL in a patient, it is desirable to assure that the patient is a good candidate for a bifocal IOL. Implantation surgery carries inherent risks to the health of the patient, as with any surgery. Additional eye surgery can also damage the eye and compromise the quality of vision after surgery. Removal of an unsatisfactory lens and replacement with a new lens subjects the patient to further risk to vision and health which may be viewed as unacceptable to both the health care professional and the patient.

Thus, there is a need for an apparatus and method for testing the ability of a subject to see properly using a bifocal IOL. In addition, there is a need for an apparatus and method to compare a subject's vision through different types of IOLs. Another need in the vision care community is an apparatus and method to monitor over months or years the geometrical and refractive configuration of an eye. The apparatus and methods of the current invention address these needs.

Bifocal corneas may be provided by inserting an inlay into the cornea of a patient. Simulating vision through a bifocal cornea is desirable for testing the ability of a subject to see properly using the bifocal cornea, and to test properties of an inlay prior to implantation. The apparatus and methods of the current invention address these needs.

There is also a need for testing IOLs and corneas generally which the apparatus and methods of the current invention address. In addition, there is a need for apparatus and methods for research and education, and for manufacturing quality control with respect to implanted lenses for the eye. The apparatus and methods of the current invention also address these needs.

SUMMARY OF THE INVENTION

The invention includes apparatus and methods for evaluating vision through an IOL. A preferred apparatus includes a human eye model having a basin or container that can hold liquid. Another component of the human eye model is a device that holds an IOL in the basin so that the IOL can be positioned to mimic the geometry and other characteristics of an eye. The human eye model also includes a cornea through which light enters the human eye model. The cornea is a lens that covers an aperture in the human eye model. The cornea can mimic the shape and optical properties of the cornea of an eye. Light enters the human eye model through the cornea, passes through the IOL, and then passes through a fovea window. The cornea, IOL, and fovea window form a collinear array whose distances can mimic the corresponding distances in the subject's eye.

The apparatus for evaluating vision through an IOL can include additional components as well. The IOL is mounted in an IOL holder. The IOL holder can include an iris cap that mimics the iris of an eye. The IOL holder can be mounted on a control mechanism such that it is moveable relative to the basin of the eye model or the cornea. The control mechanism can be mounted on a removable lid that allows ready access to the IOL in the IOL holder for changing the IOL. The cornea can be mounted on a cornea holder that forms a liquid tight seal over the aperture in the human eye model and that allows interchangeable corneas. The apparatus can also include a selection of corneas or iris caps that can be interchanged to more closely model the subject's eye. Furthermore, a selection of IOLs can be included so that the subject's tolerance of various designs of IOLs can be tested.

The human eye model can be mounted on a fovea projector. A fovea projector includes a fovea window that can be moved relative to the IOL. The fovea projector also includes an objective lens and an eyepiece that are oriented so that light entering the fovea projector through the fovea window is detectable at the eyepiece. The fovea window can fit in an aperture in the human eye model.

A method of the invention uses an apparatus simulating an eye to evaluate a subject's vision through an IOL. The method includes having a subject view symbols mounted on or near the fovea window such that these symbols are focused in the subject's vision. Then, the subject, looking through the eyepiece of the fovea projector, views sequentially one or more targets that can be at different distances from the human eye model. The subject's ability to view the targets is evaluated.

When a bifocal IOL is mounted in the human eye model, the subject's suitability for implantation of a bifocal IOL can be evaluated. A subject that is unable to view through a bifocal IOL targets at different distances corresponding to the different powers of the lens would be unsuitable for implantation of a bifocal IOL. Alternatively, IOLs of different design may be inserted in the human eye model and the subject's vision through the different IOLs can be evaluated. The IOLs can be moved, tilted, or decentered relative to the cornea or fovea window in this procedure. This allows selection of the design of IOL most suitable for the subject. In addition, through movement of the fovea window or the IOL relative to the cornea or the basin of the human eye model, dimensions or geometric constants of the subject's eye can be determined.

The method can require optimization of the position or characteristics of different components of the human eye model. The method can include changing the position of the IOL relative to the cornea or the fovea window. This can allow evaluation of the subject's vision at different geometric configurations. The method can also include evaluating the subject's vision with different iris caps or different corneas installed in the human eye model. In addition, the method can involve altering the distance between the fovea window and the IOL or the cornea.

The apparatus and methods of the invention can also include uses in model systems and for teaching. The image from the fovea window can be projected onto a screen or film, into a video display system, or other storage or display device. The image from the fovea window can be projected into the eye of a nonhuman animal. The methods and apparatus can be used for training users, for teaching vision care professionals, for clinical or pharmacological studies, for research, and the like.

In addition to evaluating and testing of bifocal IOLs, the present invention also concerns apparatus and methods for testing and evaluating bifocal corneas.

DETAILED DESCRIPTION OF THE INVENTION

Figure 1:
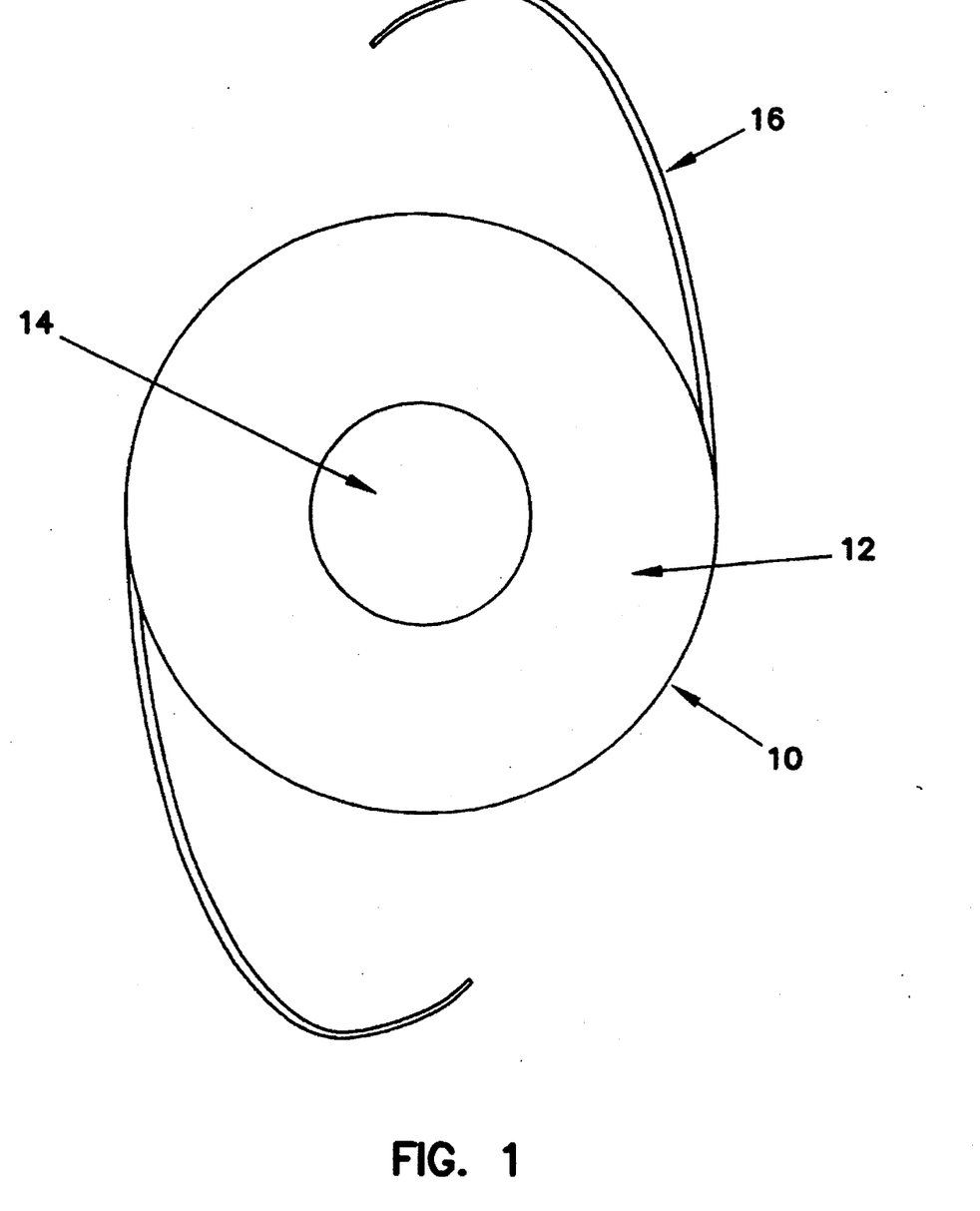
FIG. 1 is a front plan view of a coaxial bifocal IOL.

Referring now to FIG. 1, a bifocal IOL 10 has two lens portions 12, 14 of different focal lengths. Typically, bifocal IOLs have concentric lens portions with, for example, an outer annular portion 12 of one optical power and an inner circular portion 14 of another optical power. Thus, two images, one in focus and the other out of focus are projected simultaneously upon the retina. The subject's brain is then required to select and process the focused image. Unfortunately, not every person is capable of selecting the focused image, so it is desirable or necessary to test for this ability before implanting a bifocal IOL 10. Haptic members 16 project outward from the bifocal IOL 10 to allow for attachment of the bifocal IOL in the patient's eye.

Bifocal IOL 10 has properties that facilitate proper evaluation of the focused image in many people. Such an IOL typically has an inner, reading lens less than 2 mm in diameter with a difference between the power of the two lenses of at least about 3.0 diopters (D) but advantageously at least about 3.5 D. The difference in power enables the brain to more easily accomplish the image evaluation. There are configurations for bifocal IOLs other than the one shown in FIG. 1. For example, a circular lens divided into two halves along the diameter is feasible or a lens with more than two rings is possible. In all cases, there must be a substantial difference in the amount of focusing between two competing images, such as at least about 3.0 D. However, this will be different for different patients.

Figure 2:
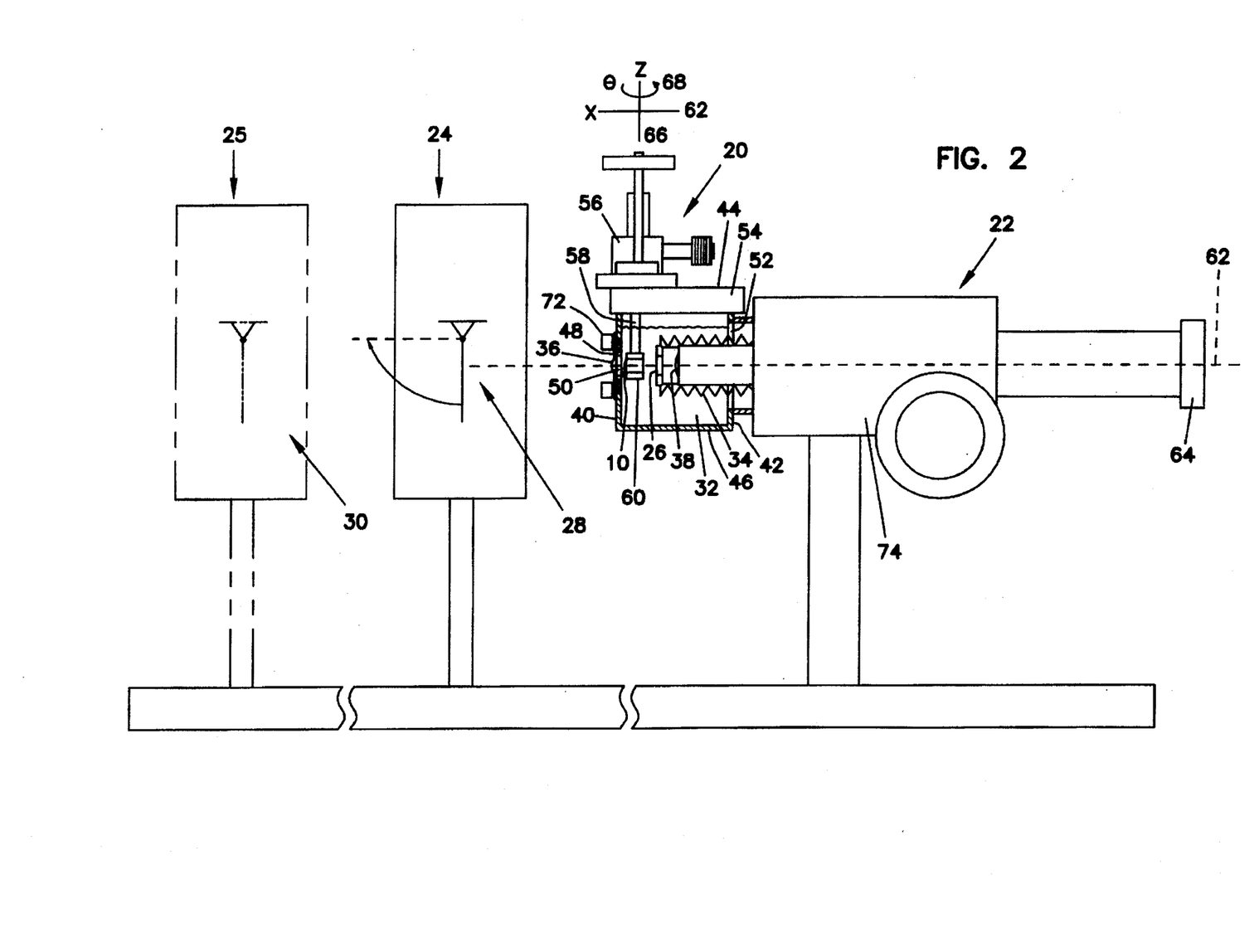
FIG. 2 is a side view of an embodiment of an evaluation apparatus according to the present invention.

Bifocal IOL 10 can be mounted in an IOL evaluation apparatus 18 shown in FIG. 2. FIG. 2 shows IOL evaluation apparatus 18, which includes a human eye model 20, a fovea projector 22, and one or more target boxes 24. Human eye model 20 is shown attached to fovea projector 22. A function of fovea projector 22 is to project an image appearing at fovea window 26 of human eye model 20 onto the fovea of the observer at a 1:1 imaging ratio. The patient will observe either a target 28 for reading vision or a target 30 for distance vision. Provisions are, optionally and advantageously, made that reading target 28 can be removed and reinserted with a minimum time delay. In some instances, it may be desirable for both reading target 28 and distance target 30 to be visible through human eye model 20 simultaneously.

Figure 3:
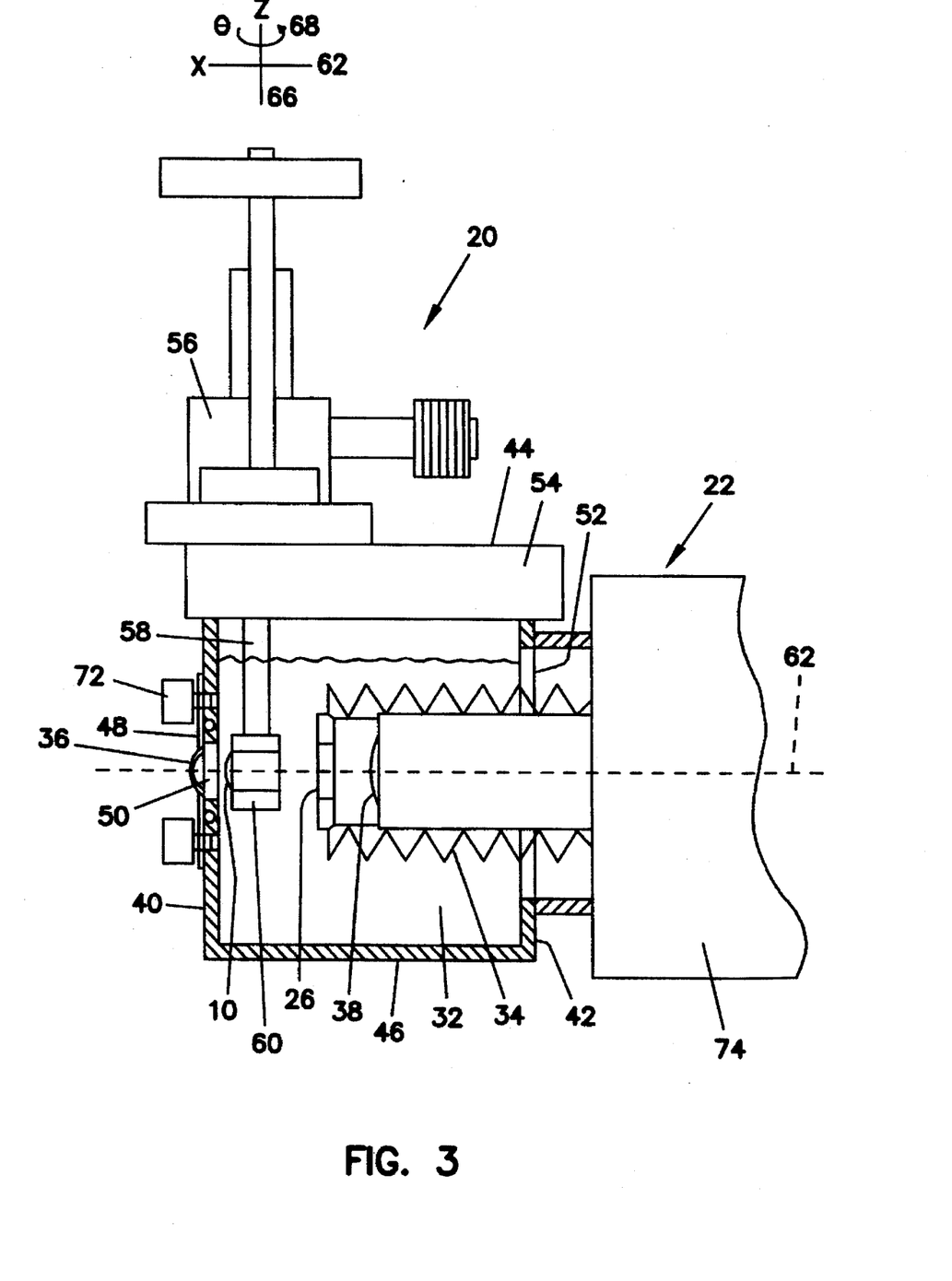
FIG. 3 is an enlarged cross-sectional side view of the human eye model mounted on the fovea projector as part of the IOL evaluation apparatus of FIG. 2.

FIG. 3 shows an enlarged view of human eye model 20. Human eye model 20 includes a basin, or other container or enclosure, 32, typically about 4 cm long, that can be advantageously filled with saline solution, preferably, having the same refractive index as the human vitreous. Seal to the outside is provided by bellows 34 and fovea window 26. In a preferred embodiment, bellows 34 allows adjustable placement of fovea window 26 at any location from about 9 mm to about 40 mm from the surface of human eye model cornea 36. The distance between fovea window 26 and objective lens 38 of fovea projector 22 is kept constant, even if fovea window 26 is moved.

Human eye model 20 is capable of mounting detachably on a fovea projector 22. Fovea window 26 protrudes into human eye model 20 with a seal between fovea projector 22 and human eye model 20 that retains water or other fluids in the basin 32 of the human eye model 20. Basin 32 of human eye model 20 can contain liquid and has several sides. The embodiment illustrated in FIG. 3 includes sides 40, 42, 44, and 46, but basin 32 may include additional sides or configurations.

A cornea holder 48 is mounted over an aperture 50 in side 40. Cornea holder 48 seals aperture 50 so that basin 32 can hold liquid above the level of aperture 50. Opposite from side 40, and typically about 4 cm from side 40, is side 42. Side 42 includes an aperture 52 that receives fovea window 26 of fovea projector 22 and bellows 34 or other mechanism that seals fovea projector 22 and fovea window 26 in aperture 52 such that the seal is liquid tight. Side 44 is adjacent to side 40 and in a preferred embodiment includes a removable lid 54. Side 44 also includes a control mechanism 56 that controls the position of IOL holder 60 and a stem 58 that links control mechanism 56 and IOL holder 60. Stem 58 projects into basin 32 and supports IOL holder 60, typically at one end of stem 58.

When human eye model 20 is mounted on fovea projector 22 as shown in FIG. 3 and control mechanism 56 is adjusted appropriately, the following components of human eye model 20 are in a collinear configuration: cornea 36 in the cornea holder 48, an IOL in IOL holder 60, and fovea window 26. This collinear configuration defines an x-axis 62. Typically, fovea window 26 and eyepiece 64 of fovea projector 22 are also on x-axis 62. Alternatively, the light path from fovea window 26 to eyepiece 64 of fovea projector 22 is not linear but instead is formed using one or more prisms, mirrors, or lenses such that light that enters through cornea 36 forms an image that can be seen through eyepiece 64 of fovea projector. When control mechanism 56 is adjusted appropriately, IOL holder 60 is between cornea 36 and fovea window 26. Measurements of dimensions of the human eye model are typically made using as a reference point the convex apex of cornea 36 as 0 mm. From this reference point in a typical version of the human eye model, cornea 36 meets cornea holder 48 at about 0.6 mm, IOL holder 60 is at about 5.6 mm, and fovea window 26, which is continuously adjustable in position over a wide range, is at about 24.0 mm.

Control mechanism 56 is mounted on side 44 (as shown in FIG. 3) in a manner such that it can controllably move stem 58 relative to side 44 and basin 32 to control the position of IOL holder 60. Control mechanism 56 anchors and manipulates stem 58. Stem 58 also is linked to IOL holder 60. Advantageously, control mechanism 56 controllably positions IOL holder 60 and stem 58 along x-axis 62 from cornea 36 to fovea window 26, along z-axis 66 perpendicular to both x-axis 62 and side 44, rotationally about z-axis 66 at an angle theta 68, and optionally along a y-axis 70, which is perpendicular to both x-axis 62 and z-axis 66. In a preferred embodiment of the invention, control mechanism 56 is mounted on a lid 54 to basin 32 of eye model 20. In this case, insertion of IOL 10 is easily accomplished by removing lid 54 including control mechanism 56 from eye model basin 32. The position of lid 54 can be reproducibly set by a mechanism that assures that lid 54 sits in only one location, such as locator pins on the basin.

Figure 5:
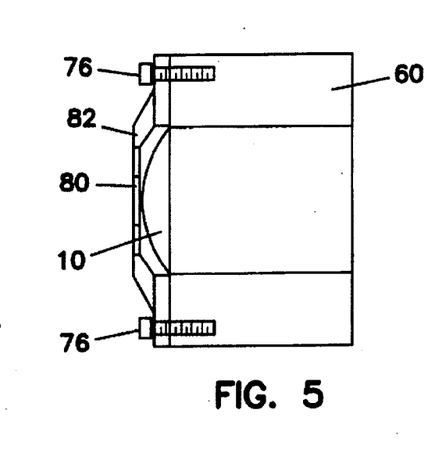
FIG. 5 is an enlarged cross-sectional side view of the IOL holder with the attached iris cap and the IOL in place.
Figure 7:
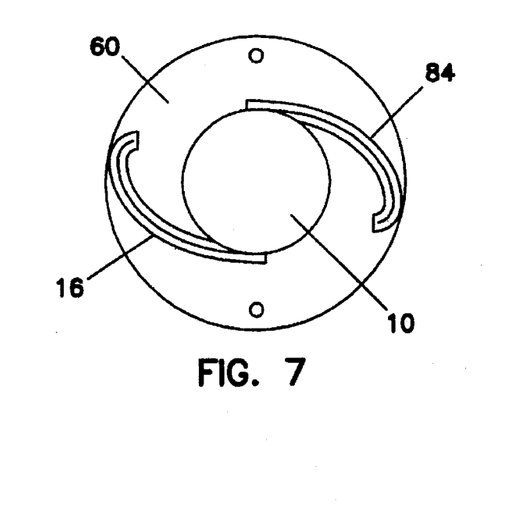
FIG. 7 is an enlarged front view of the IOL holder with the iris cap removed and the IOL in place.
Figure 8:
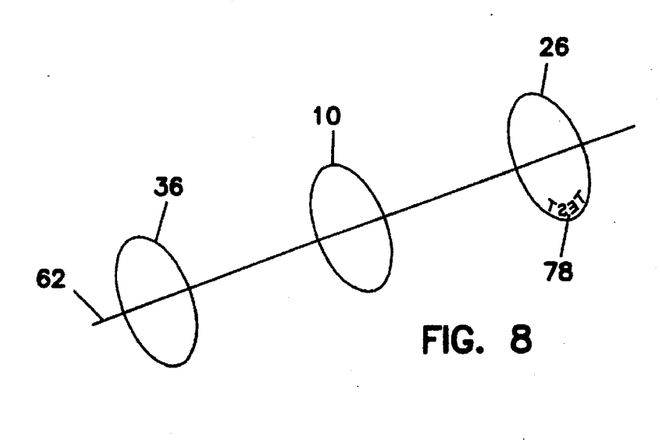
FIG. 8 is a perspective schematic view of the cornea, the IOL, and the fovea window.

FIG. 5 shows a cross-sectional side view of IOL holder 60. IOL holder 60 mounts, preferably detachably, on stem 58. An IOL in IOL holder 60 can be positioned between cornea 36 and fovea window 26 allowing light to project through cornea 36, an IOL in IOL holder 60, and fovea window 26. IOL holder 60 allows for secure positioning of IOL 10 in IOL holder 60. In a preferred embodiment, haptic members 16 of IOL 10 are positioned in recessed areas 84 of IOL holder 60, as shown in FIG. 7.

Figure 6:
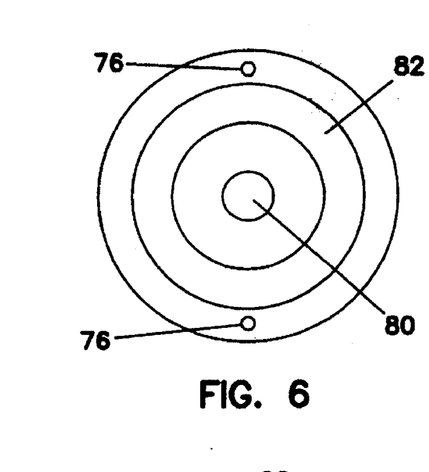
FIG. 6 is an enlarged front view of the IOL holder with the iris cap in place.

IOL holder 60, optionally, includes an arrangement for mounting an iris cap 82 adjacent to IOL 10. The mounting arrangement as shown in FIGS. 5 and 6 includes threaded, screw-like fasteners 76 that fasten iris cap 82 to IOL holder 60, but other fasteners will work as well. Iris cap 82 provides an aperture 80 through which light can pass that is of smaller diameter than the IOL 10 (FIG. 5). This mimics the structure of the human eye in which a variable iris is smaller than the lens. The mechanical iris of the human eye model need not be adjustable since detachable iris caps 82 with different sized apertures can be interchanged on IOL holder 60. However, an adjustable iris cap may be used.

Preferably, IOL holder 60 can be moved along x-axis 62, z-axis 66 and, optionally, y-axis 70, as well as rotated about angle theta 68. Displacement along x-axis 62 is used to position IOL 10 the proper distance from cornea 36. Movement along z-axis 66 and, optionally, y-axis 70 mimics decentering of the lens. Movement through theta angle 68 simulates tilt. All of these manipulations can be accomplished while IOL 10 is submerged or in place and the patient is observing. The settings of the manipulators can be sensed by standard optical encoders or other sensors. Optical encoders sense the position of the IOL or the setting of control mechanism 56. The position settings are then fed into a computer for recording and analysis, advantageously, along with other data for the patient.

Light enters human eye model 20 through aperture 50 in side 40. During use, human eye model 20 is filled with liquid above aperture 50 in side 40, so aperture 50 must be covered or filled with transparent material that forms a liquid tight barrier with side 40 of human eye model 20. For example, aperture 50 could be filled with a transparent plastic or glass plug. Alternatively, a lens could be fitted in or over aperture 50 with an appropriate apparatus for forming a seal around the aperture.

Figure 4:
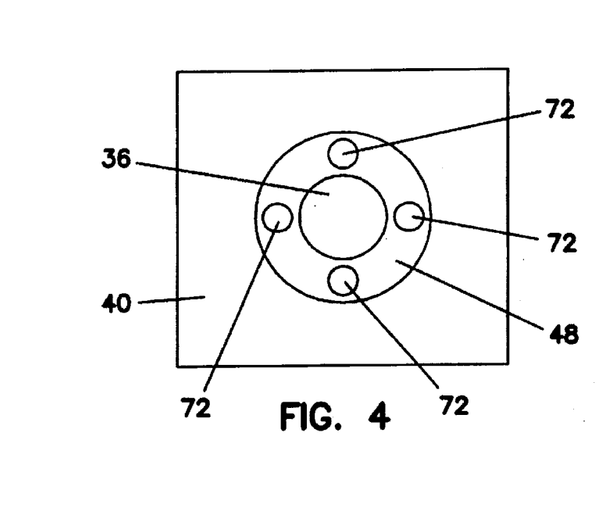
FIG. 4 is an enlarged front view of the cornea holder with the cornea in place.

In a preferred embodiment of the invention, aperture 50 is sealed by a cornea 36 in a cornea holder 48. Cornea holder 48 and cornea 36 are shown attached to human eye model 20 in FIG. 3. A front view of cornea holder 48 and cornea 36 on basin 32 of human eye model 20 is shown in FIG. 4.

Cornea holder 48 mounts on side 40 of human eye model basin 32. Cornea holder 48 mounts over aperture 50 of basin 32 that allows light to enter the basin 32 along x-axis 62. Cornea holder 48 includes fasteners 72 that attach cornea holder 48 to basin 32 of human eye model 20. When mounted, cornea holder 48 forms a liquid-tight junction with basin 32 so that basin 32 retains liquid. Preferably, cornea 36 and cornea holder 48 combine to form a convex surface approximating the surface of an eye.

Cornea 36 is a lens which preferably approximates optical properties of the cornea of the subject's eye or of a typical eye. Preferably, cornea 36 also approximates the shape of a cornea of a human eye. Cornea 36 is easily removed from and replaced in cornea holder 48. Corneas 36 having different optical powers and different astigmatic afflictions are included in the invention. Such corneas 36 can be supplied as a set that facilitates practicing the method of this invention. Typically, the shape of the patient's cornea is known prior to using the invention.

Fovea projector 22 produces an enlarged (between about 10x and about 20x) rear image which is observed by the patient through an eyepiece 64. Fovea projector 22 includes in a collinear array fovea window 26, objective lens 38, and eyepiece 64. An image or light entering through fovea window 26 passes through objective lens 38 to eyepiece 64 where it can be perceived or detected. Alternatively, fovea window 26, objective lens 38 and eyepiece 64 are not in a linear array, but light is guided between them by one or more prisms, mirrors, or lenses. Components of the fovea projector are supported by fovea projector body 74. Fovea projector body 74 is opaque and light tight such that movement of fovea window 26 or eyepiece 64 relative to the rest of fovea projector body 74 occurs without light entering fovea projector body 74 other than through eyepiece 64 or fovea window 26. Fovea projector 22 can be mounted on a device that allows it to be moved vertically and horizontally.

Fovea window 26 has small letters or symbols 78 engraved or otherwise mounted or supported on its surface, preferably the anterior surface. Advantageously, the letters are engraved on the anterior surface. Preferably, letters or symbols 78 can be illuminated, preferably when the view of the target is blocked.

Movement of fovea window 26 relative to eye model 20 or fovea projector body 74 can be accomplished by a variety of methods including sliding as in a simple telescope, a screw and gear system, or other positioning apparatus such as is used in a microscope, a telescope, binoculars, or another optical device. The positioning apparatus and fovea projector body 74 optionally detects and relays the position of the fovea projector window to an external recording device.

Target 28 is, typically, positioned at standard reading distance from human eye model 20 and fovea window 26. It is positioned along x-axis 62 that extends from fovea projector eyepiece 64 through human eye model 20. Readable target 28 can be of any type commonly used in testing vision. Preferably, target 28 is mounted in target box 24. Target box 24 supports target 28 and, advantageously, allows target 28 to be quickly and easily removed from the imaging field of human eye model 20. For example, target 28 can be rapidly flipped upward out of the imaging field. Moving target 28 allows a viewer at fovea projector eyepiece 64 to see through target box 24 to target 30 at greater distance. The apparatus can, optionally, include target 30 and, possibly, target box 24 about twenty feet from the human eye model. Then the apparatus can test vision at a greater distance.

Both target boxes 24 and 25 may, optionally, include a lighting system for illuminating the target. In addition, targets 28, 30 or target boxes 24, 25 can include an apparatus that allows the position of the target or target box to be adjusted both horizontally and vertically.

The apparatus can include human eye model 20 mounted on fovea projector 22 so that cornea 36, IOL holder 60, and fovea window 26 are in a collinear array. Through fovea projector eyepiece 64 a subject can view target 28 at reading distance and a target for distance viewing 30 as well. To use the apparatus for evaluating an IOL, an IOL 10 is mounted in IOL holder 60 and control mechanism 56 is used to adjust the position of IOL 10 between fovea window 26 and cornea 36.

The apparatus described above is useful since prior to surgery to implant an IOL it is desirable, even necessary, to evaluate a patient's ability to process the focused image from a bifocal IOL 10. The invention includes methods to accomplish such evaluation. Evaluation, preferably, is done years before a patient requires cataract surgery while the patient's vision is still good. Screening would be repeated until the surgery becomes necessary. This screening would allow the ophthalmologist to recommend implanting a bifocal IOL or another IOL. It is important to screen out patients that cannot handle a bifocal IOL, since in such cases an implanted bifocal IOL may have to be removed. This repetitive eye surgery is potentially damaging and undesirable.

Usually both eyes do not become afflicted with cataract at the same time. In cases when surgery becomes necessary without having prior yearly screenings performed, it is therefore sufficient to use the eye that is not yet afflicted by cataract for testing the patient's compatibility for a bifocal IOL. This is possible since actually the brain is tested rather than the eye.

The screening method, like a bifocal IOL, produces two superimposed images in the patient's eye, one for reading and the other for distance vision. As with an implanted IOL, one image is always out of focus. The image evaluation system of the brain will try to select the focused image. Unfortunately, not all people are alike and the brains of some patients cannot produce the correct evaluation of the focused image. These patients then experience double lines instead of edges.

While an important concern is to screen patients to ensure that a bifocal implant is appropriate for them, screening can also allow the ophthalmologist to compare lenses of different design and different make to be able to give the best advice to his/her patients. This is significant, since without such screening the patient and physician have no method to determine the lens most suitable for implantation. Currently, only after implantation can the physician test for acuity or interview the patient about poor color performance or lens aberrations. However, after implantation any remedial steps require additional and potentially damaging eye surgery.

Furthermore, the medical community should find it useful to record the changes in the geometrical and refractive configuration of the patient's eye over the lifetime of the patient. The present invention can be sufficiently automated to produce records of this kind within a few minutes. In this case, it can be used for all patients regardless of whether or not a bifocal implant is anticipated. Such an apparatus and method are required to gather more information about the subject's vision than can currently be obtained from tests and patient interviews. This apparatus and method can then increase the success rate for implantation of bifocal IOLs.

A method of the invention includes various steps described in the following paragraphs. In carrying out this method, it is assumed that the geometrical dimensions of the patient's eye are known. Then, for example, the distance between IOL 10 and fovea window 26 are set to equal this distance. However, for many purposes a typical or average distance may be chosen. For other purposes the geometry of the patient's eye can be determined by standard methods.

The subject must be able to focus on fovea window 26. The fovea window 26 is illuminated from the outside by a suitable light source, while the view of target 28 is blocked, for example, by a suitable shield. Fovea window 26 has small letters or other symbols or images 78 on or near its surface. The letters, symbols, or images 78 are preferably engraved on fovea window 26 but they can be mounted or supported on or near the surface of the fovea window. The size of letters, symbols, or images 78 are chosen to be the smallest size the subject can be expected to read or discern. The subject is asked to manipulate fovea projector eye piece 64 distance until they can read letters, symbols, or images 78 on fovea window 26. After this is accomplished, fovea window 26 and IOL holder 60 are placed at a distance believed to represent the corresponding distance in the subject's eye.

For evaluating suitability of a bifocal IOL 10 the following is carried out. The subject is asked to read the reading target 28. If the subject is no longer capable of accommodation, the subject's eye is still focused on the anterior side of fovea window 26. The subject's eye will, therefore, relay in a 1:1 relationship to their own fovea whatever appears on the fovea window. If the subject is capable of selecting the focused image they can read reading target 28 properly. Next, distance vision can be tested. To test distance vision, reading target 28 is temporarily removed and the subject is asked to read the distance target 30. Alternatively, the subject can first read the distance target 30, then reading target 28 is inserted in the patient's field of view.

Under these conditions the subject is exposed to two superimposed images stemming from two lenses of bifocal IOL 10, one of these images being unfocused and the other focused. If the subject can accommodate, their brain can select the focused image. If the subject can read the target shown second, it is proper to conclude that the bifocal IOL can be successfully implanted.

If the subject cannot read one or both of the targets properly, fovea window 26 was, possibly, not placed in the proper location. Therefore, if an improvement in the subject's vision can be made by moving fovea window 26, the geometrical constants of the subject's eye should be remeasured. Another possibility is that the distance from cornea 36 to IOL 10 is incorrect. In this case, movement of IOL 10 along x-axis 62 should provide improvement. Still another possibility is that an inappropriate cornea 36 was selected. That can be checked by replacing cornea 36 with a slightly different one, for example cornea 36 of a slightly different power or shape.

A main concern, of course, is that IOL 10 may be properly selected. The design of the simulator sees to it that it is convenient to remove and insert IOLs 10 in the IOL holder 60. In a preferred embodiment of the invention, this can be accomplished by removing lid 54 including control mechanism 56 from eye model basin 32, inserting a different IOL 10, and reinserting the assembly. Locator pins ensure that the lid is placed in the same location as it was before, in this preferred embodiment. A variety of IOLs can be tested until a satisfactory match is found between subject and IOL.

When an apparently suitable IOL 10 has been selected, the subject's tolerance to the geometry of the implant can be tested. For example, the operator can decenter IOL 10 until the subject can no longer perform at both distance vision and reading vision. Decentering includes displacement along z-axis 66 and y-axis 70. Also, rotation through angle theta 68 can explore how much tolerance for tilt exists. Obviously, tolerance for all the mentioned displacements will be different for different patients and different lens designs. If there is an indication that only small tolerance exists for any of these displacements, the operator may want to test the patient on a monofocal implant, to determine if better tolerance exists. This enables the vision professional to form a well rounded professional opinion as to what kind of implant he should prescribe for the patient. Once a satisfactory match between subject and IOL has been achieved and the vision professional is satisfied that the geometrical constants of the patient's eye have been properly simulated, the prescription of the IOL can be certified.

An ophthalmologist or other eye or vision care professional can use the simulator to compare the performance of lenses of different design. In this case, the observer may be young enough to be able to accommodate. Therefore, the observer's eye will focus on the correct image by accommodation rather than by the brain restoring the image by image evaluation. An optical professional can prevent this. For example, the subject can concentrate on letters, symbols, or images 78 on the fovea window 26 so that they are readable and in focus. This causes the accommodation mechanism to focus on the anterior surface of fovea window 26 and, therefore, acquires any image as it appears on this location. In other words, the subject will "see" with the IOL.

The procedure described above assumes that all geometrical constants of the patient's eye are known. Of course, they can be measured and the procedure as described above can then be performed. Alternatively, the apparatus and method of the invention can be used for screening subjects to ascertain whether their brains are capable of the image evaluation required to use a bifocal IOL. For this purpose it is not necessary, at least initially, to use the exact dimensions of the subject's eye. It will be sufficient to use the measurements of the standard eye and use the appropriate IOL 10 for this eye. What appears on fovea window 26 is an image which is defocused to a degree that is typical. If the subject can handle this situation, then this is an indication that he will be able to handle a bifocal IOL unless his eye dimensions deviate considerably from normal. Also, considering that the dimensions of the eye will change with advancing age, it may be advantageous to wait with obtaining the patient's eye dimensions until near the time when cataract surgery is required.

With this approach the screening procedure becomes fairly simple, a matter of a few minutes. However, the ophthalmologist may decide to take the time to record the fovea window settings. Since the fovea projector performs a 1:1 image on the patient's fovea a change in the setting of the fovea window, required by the subject to see well, indicates that the subject's eye geometry has changed as well. Changes from year to year are to be expected, however, extreme changes may indicate the onset of glaucoma.

The methods and apparatus of the invention can also be used for research and pedagogical purposes. For example, the image from the fovea window can be projected onto a screen, wall or other surface. This can be useful for teaching vision care professionals or others aspects of the methods and apparatus, aspects of the design and manufacture of intraocular lenses, and the like. Furthermore, the image from the fovea window can be projected onto film, a video camera, or like devices for storage and analysis of the image. With an appropriate lens or prism arrangement, such projection can occur simultaneously with a subject viewing the image at the fovea projector eye piece. Projection of an image from the fovea window into the eye of a nonhuman animal allows pharmacological, experimental, or clinical studies of image detection and vision.

Figure 9:
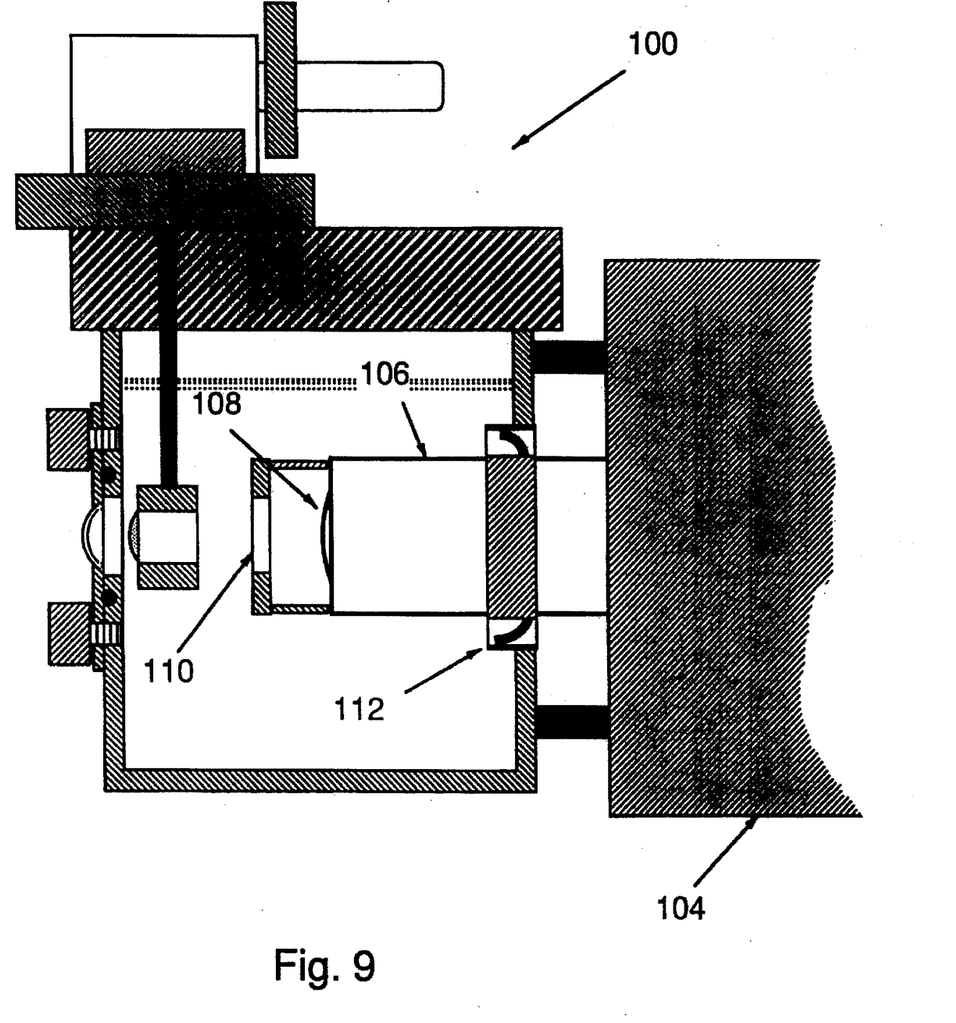
FIG. 9 is a side view of an alternative embodiment of an evaluation apparatus according to the present invention, including a shaft seal instead of a bellows.

Referring now to FIG. 9, a modified evaluation apparatus 100 is shown including a basin 102, a fovea projector 104, and a moveable shaft 106 carrying an objective lens 108 and a fovea window 110. A shaft seal 112 seals shaft 106 of fovea projector 104 relative to basin 102. Shaft seal 112 is an alternative seal arrangement over bellows 34.

Figure 10:
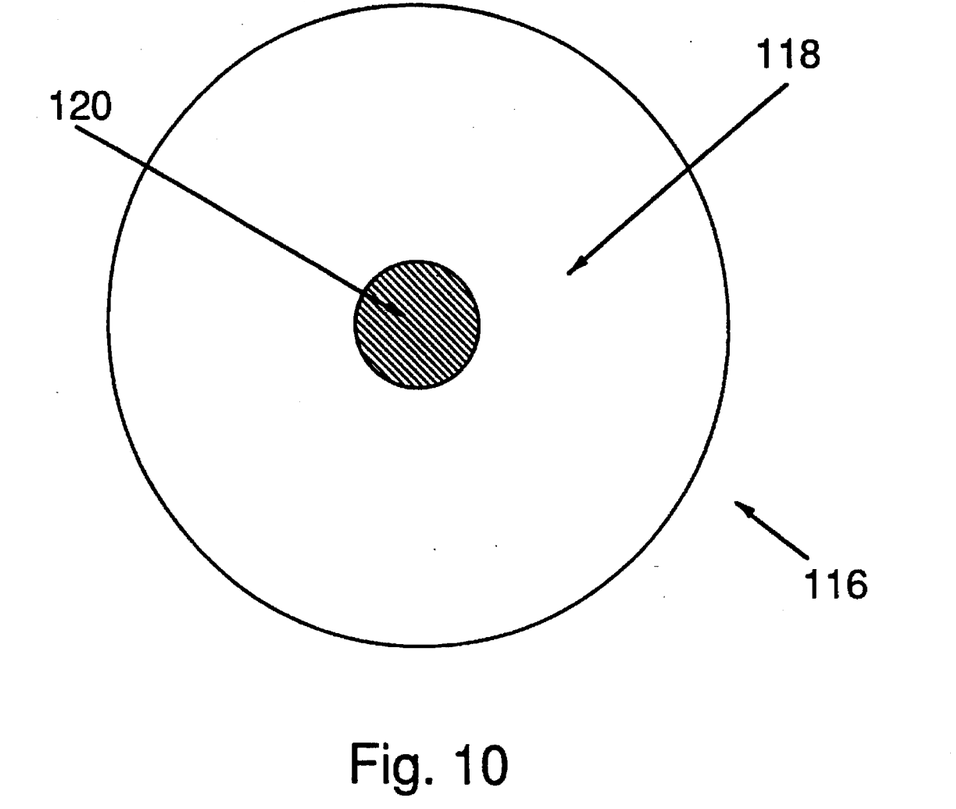
FIG. 10 is a front plan view of a coaxial bifocal cornea.
Figure 11:
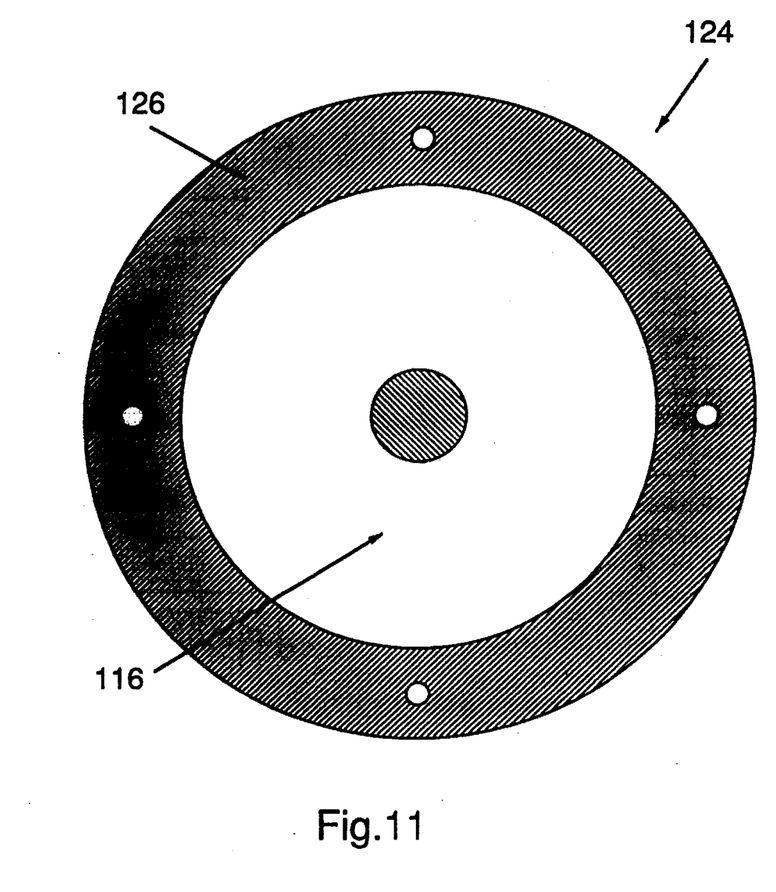
FIG. 11 is a front view of a bifocal cornea mounted to a cornea holder.
Figure 12:
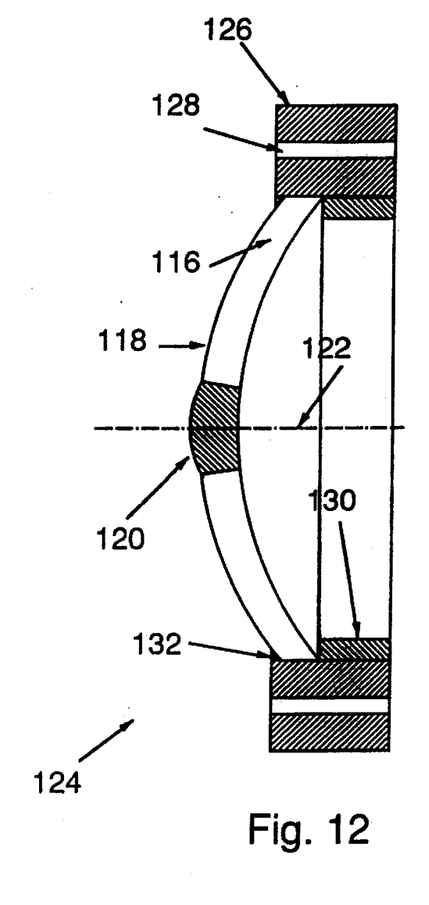
FIG. 12 is a cross-sectional side view of the cornea and cornea holder of FIG. 11.

Referring now to FIGS. 10–12, a bifocal cornea 116 and a cornea holder 124 are shown. Cornea holder 124 is constructed like cornea holder 48 described above. Cornea holders 48, 124 hold the corneas 36, 116 for mounting to basins 32, 102. Bifocal cornea 116 includes a distance portion 118, and a reading portion 120. Both distance portion 118 and reading portion 120 are coaxial along axis 122 of bifocal cornea 116. Cornea holder 124 includes an outer support ring 126 including holes 128 for fasteners 72 as described for apparatus 18. Cornea holder 124 further includes an inner support ring 130 mounted to outer support ring 126. An outer periphery 132 of bifocal cornea 116 is preferably adjacent to both outer support ring 126 and support ring 130, and is glued or otherwise attached thereto. In this manner, bifocal cornea 116 and cornea holder 124 form a single unit which can be mounted to basin 32, and removed therefrom to be replaced by another holder with another cornea mounted thereto. The construction of cornea holder 124 can be useable with other corneas, such as single power cornea 36 described above.

In the case of a bifocal cornea, a similar result for the patient is desired as with a bifocal IOL. The patient views through both portions of the cornea simultaneously when a bifocal cornea is present in a patient's eye. The useable power differential between the distance portion 118 and the reading portion 120 is in the range of +1.5 diopters (D) to +5.0 D, with +3.0 D common for many patients. As with bifocal IOLs, the patient will see through both parts of the bifocal cornea and therefore will receive two different images, one of the two being blurred. It is expected that the brain of the patient will discriminate against the wrong image. Therefore, it is a purpose of apparatus 18 to test patients prior to performing an operation to inlay a reading lens portion, like reading lens portion 120, into the cornea of the patient to create a bifocal cornea. The use of apparatus 18 will indicate to the physician or other eye care specialist whether or not the patient's brain will be able to discriminate against the wrong image, in much the same manner as bifocal IOLs are tested as noted above.

Since the cornea of the patient is made bifocal by inserting an inlay, and since the human cornea is flexible, there is a possibility that the mechanical properties of the cornea are altered by the inlay and by the healing process after insertion of the inlay. Following implantation of the inlay, the cornea may react differently to the internal pressure of the eye than prior to implantation surgery. Under the internal pressure of the eye, the cornea may have a different shape following the implantation surgery. The consequence could be that merely an additional change in power, not related to the power of the inlay, is experienced. An increase in power is the purpose of the inlay operation, but the increase in power obtained could be more than expected. More importantly, the achieved distortion of the surface of the cornea could be unsymmetrical. Such nonsymmetry could be caused by placing the inlay off-axis or just by the way the cut for the insertion was made. In the case of nonsymmetry, the brain of the patient would most likely correct for this deficiency (within limits). This may be true for most patients, but not for all. Therefore, a screening of patients could be done to find those who cannot cope with a moderate unsymmetrical distortion.

Figure 13:
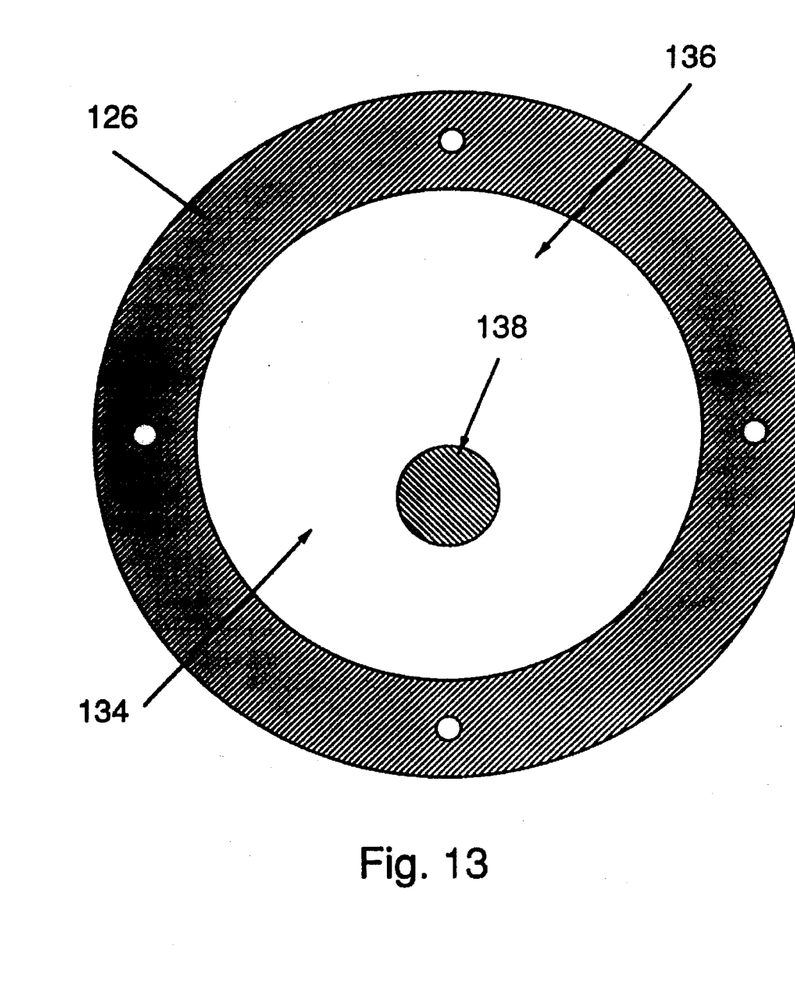
FIG. 13 is a front view of an alternative cornea having the second lens portion mounted off center.
Figure 14:
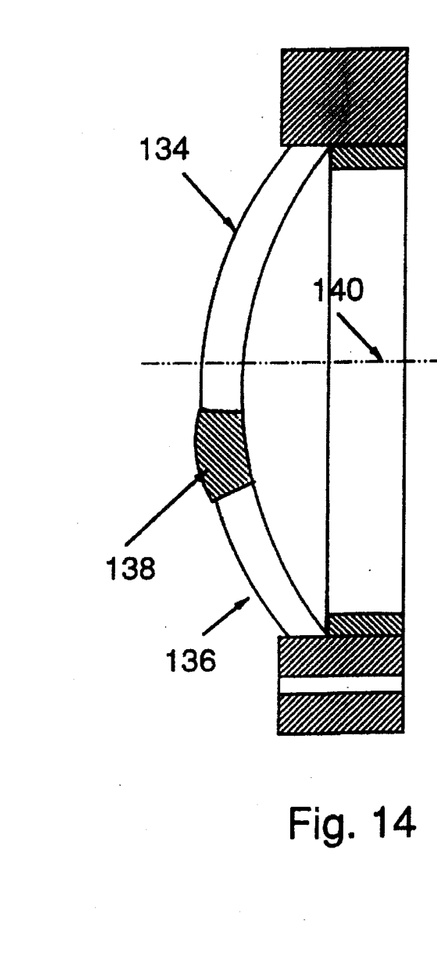
FIG. 14 is a cross-sectional side view of the cornea and cornea lens holder of FIG. 13.

To simulate this distortion, one can provide for apparatus 18 various bifocal corneas 116 having the inlay off-axis. An example bifocal having an off-axis mounting arrangement is shown in FIGS. 13 and 14 for off-axis bifocal cornea 134. Distance portion 136 is constructed in a similar manner as distance portion 118, except that reading portion 138 is mounted off-axis from axis 140 of distance portion 136.

Figure 15:
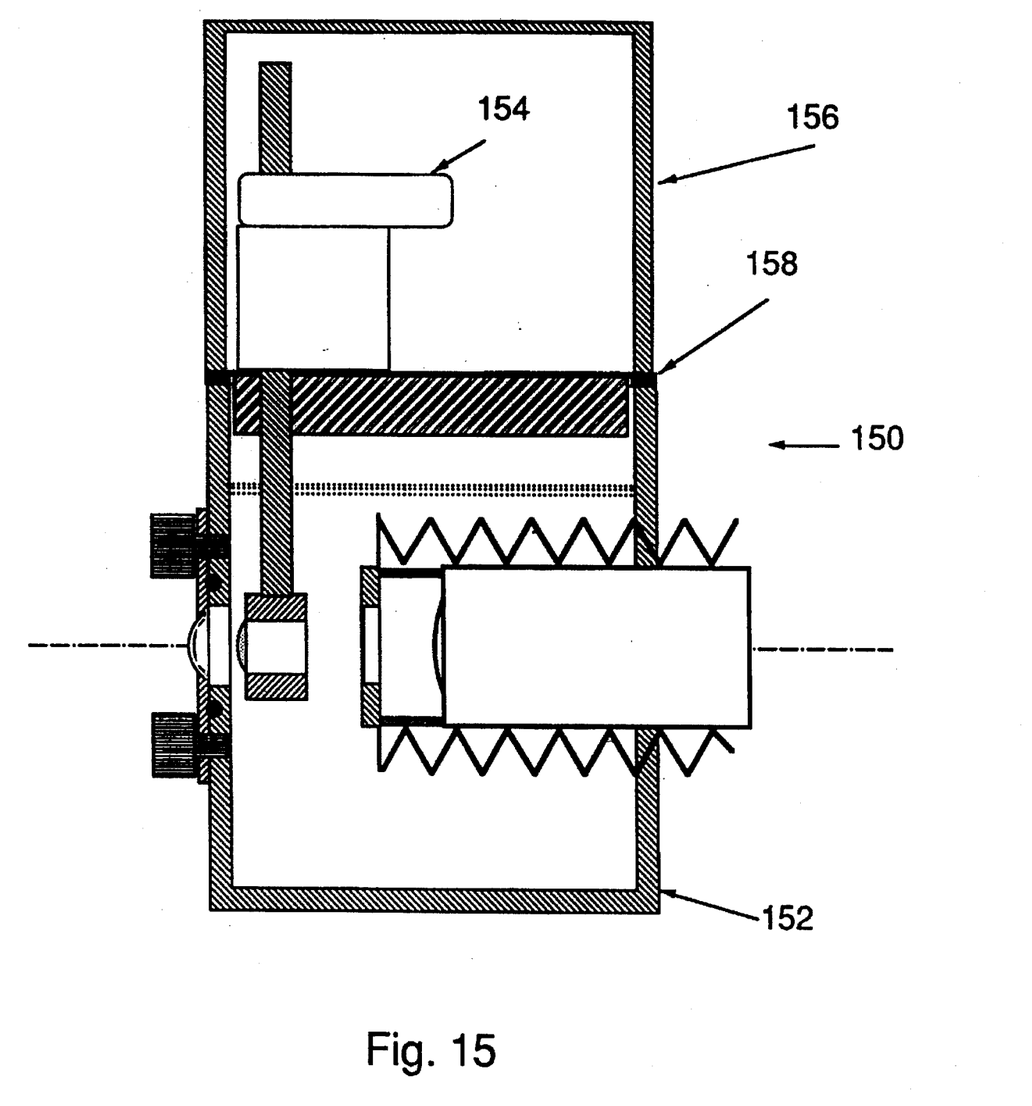
FIG. 15 is a side view of an alternative embodiment of an evaluation apparatus according to the present invention for pressurizing the liquid filled basin.

An alternative apparatus 150 is shown in FIG. 15 for testing and evaluating vision through a bifocal cornea and includes a construction which allows for pressurization of basin 152. Control mechanism 154 is modified to fit within a cover 156 which is sealed to basin 152 with a seal 158. By placing air tight cover 156 over basin 152 apparatus 150 can be pressurized, as a human eye is. A cornea is selected of a material which is flexible, such as silicone or silastic or other suitable transparent flexible plastics. In apparatus 150, part of the bifocal cornea would be off-axis. Then, by applying various pressures to apparatus 150 one could vary the degree of distortion while the patient is viewing. The limitation of tolerance for distortion could be explored for each patient before the operation. This would provide the physician a chance not to operate on patients who have little or no tolerance to distortion.

Figure 16:
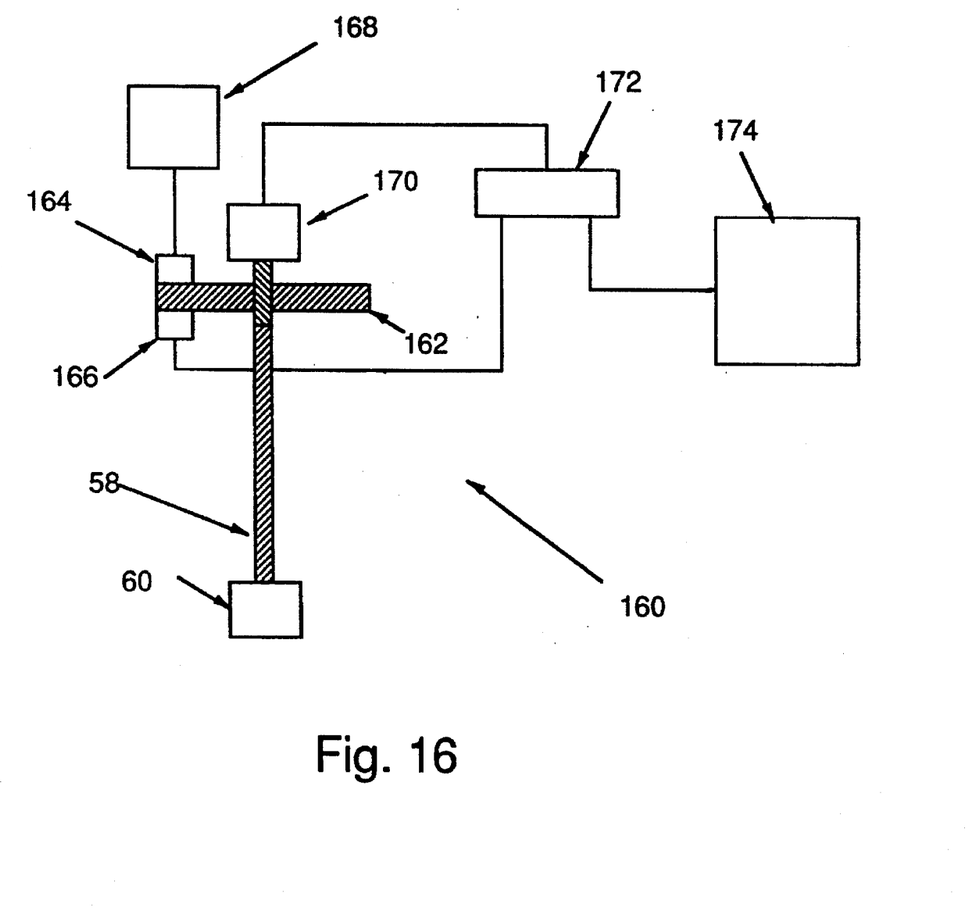
FIG. 16 is a block diagram of a control system of one of the drives of the control mechanism for moving the IOL relative to the basin.

Referring now to FIG. 16, an example position sensor 160 for control mechanism 56 is shown for sensing the position of IOL holder 60. Such position sensor 160 allows for automated control and recording of testing and evaluation procedures of apparatus 18. Position sensor 160 is used to measure the position of IOL holder 60 along the x-axis. Additional control systems constructed in a similar manner can be provided with respect to controlling and recording movement and position with respect to the z-axis movement, angle theta movement, and y-axis movement, if provided. Control system 160 shown in FIG. 16 includes an optical encoder 162, a light source 164 and a photo diode 166. A power supply 168 powers light source 164. A stepping motor 170 moves shaft 58 and optical encoder 162. This movement results in movement of IOL holder 60. Stepping motor 170 is controlled by stepping motor drive 172, which is linked to computer 174.

Figure 17:
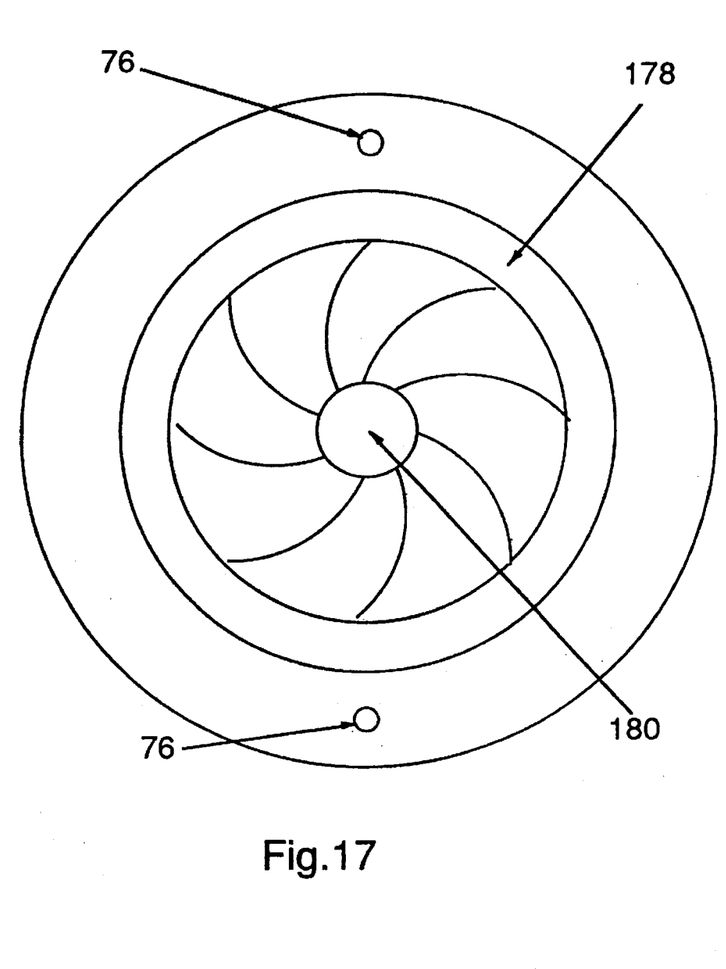
FIG. 17 is a front view of an alternative embodiment of the IOL holder with a variable diameter iris cap in place.

The various apparatus described above allow placement of either an IOL (a bifocal or single focal) or a cornea (a bifocal or a single focal) off-axis. The various apparatus also allow rotation of the IOLs. The operator can explore the effects of these distortions. It is also possible to test the tolerance for defocusing, meaning the lens is not positioned at the correct distance from the fovea. There is a depth of field for any lens that allows some error in placement of the lens. This depth of field can be adjusted by the opening of the iris. The smaller the iris generally the larger the depth of field. For this application, an iris cap 178 as shown in FIG. 17 can be provided. Iris cap 178 includes a variable aperture 180 somewhat analogous to a photographic camera. Control mechanism 56 described above, could be linked to control the aperture size of variable aperture 180.

Figure 18:
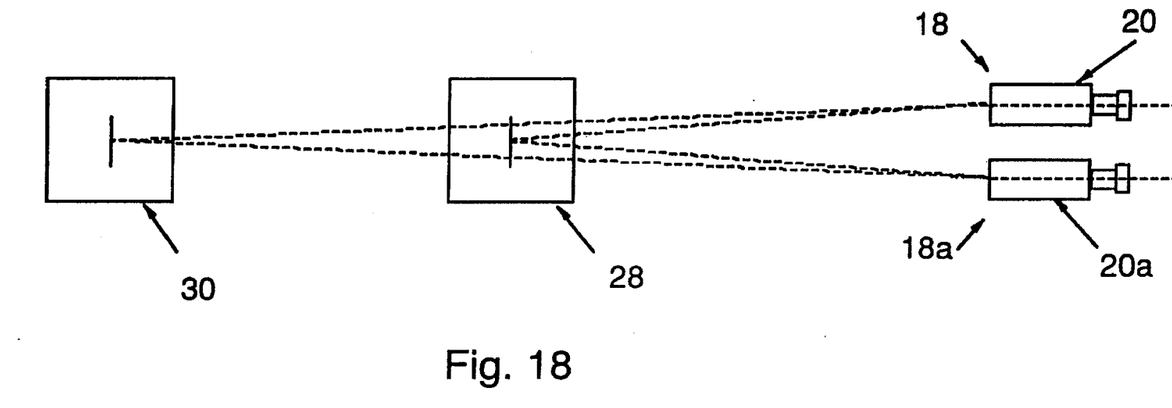
FIG. 18 is a schematic top view of two evaluation apparatus according to the present invention to achieve a binocular effect.

Referring now to FIG. 18, two evaluation apparatus 18, 18a including human eye models 20, 20a are provided for viewing targets 28, 30. The arrangement of FIG. 18 allows for binocular type viewing, one human eye model 20, 20a for each eye of the patient or other person viewing through human eye models 20, 20a.

Figure 19:
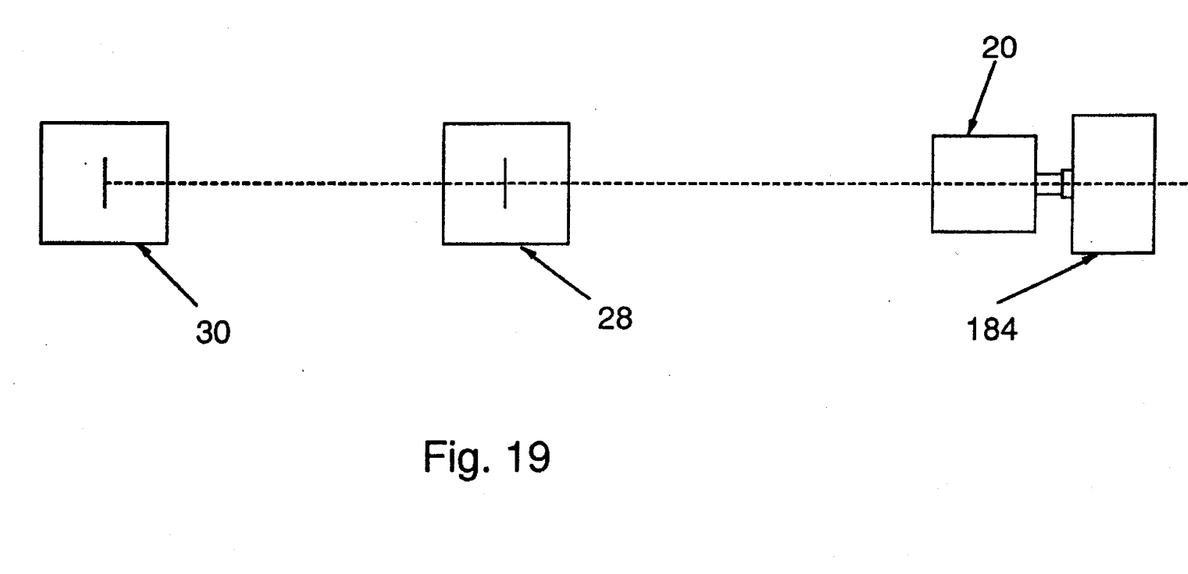
FIG. 19 is a schematic side view of an evaluation apparatus according to the present invention where the results are recorded by a camera.

Referring now to FIG. 19, use of human eye model 20b is shown in use for viewing targets 28, 30 wherein the light is received by a camera 184, such as a T.V. camera or a digital still camera. In this case a modification of the fovea projector magnification is desirable so that the image viewed is matched to the size of the detectors in the focal plane array the camera uses for producing the same resolving power of the human eye. The fovea projector would be provided with about twice the magnification one would use for a human observer. For these types of applications, the change in point spread and line spread function and the change in contrast sensitivity of the distorted optical system is tested rather than the ability of the brain to discriminate against a blurred image. Therefore, it is advantageous to digitize the image and interrogate the digitized image with computer programs relevant to image evaluation. The digitizing is accomplished by either using a digital still camera or in the case of the T.V. camera, by using a frame grabber.

Figure 20:
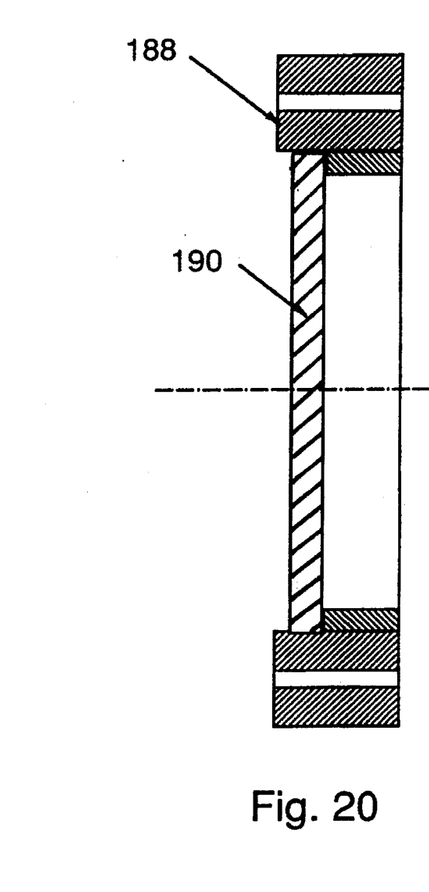
FIG. 20 is a side view of a cornea with zero power mounted to a cornea holder for use in a submerged optical bench.

A further modified apparatus can be useable in a submerged optical bench to check the quality of the lenses during production. The measurements can be made with respect to focal length (optical power), point spread, and line spread function, and the produced scatter plot. In this case, a cornea 190 of zero optical power would be used, such as shown in FIG. 20. Cornea 190 is mounted to holder 188 and has a planar shape.

The optical practitioner can easily compare the performance of IOLs of different manufacturers before they are implanted into patients. A patient cannot make such a comparison since the patient will not know after implantation how well he would have seen with a lens made by a different manufacturer. To test the inlays of different manufacturers, a flexible cornea could be used that has the same refractive index as the human eye. The inlays would need to be placed in this artificial cornea (or possibly a cadaver cornea) by the same surgical procedure as used in the actual operation. The obtained optical component can be tested in the apparatus and different makes of inlays can also be compared.

The invention has been described with reference to various specific and preferred embodiments and techniques. However, it should be understood that many variations and modifications may be made while remaining within the spirit and scope of the invention.

What is claimed is:

1. A vision simulating apparatus comprising:

a basin with a chamber for holding liquid;

a cornea mount for holding a cornea and allowing light to enter the basin;

an intraocular lens holder positioned in the chamber; and a fovea window allowing light to exit the basin wherein the cornea mount, the intraocular lens holder and the fovea window are arranged such that light entering the basin at the cornea mount passes through the intraocular lens holder before leaving the basin at the fovea window.

2. The apparatus of claim 1 further comprising an iris cap mounted between the intraocular lens holder and the cornea mount, the iris cap defining a central aperture.

3. The apparatus of claim 2 comprising a variable iris cap defining the central aperture wherein a diameter of the central aperture can be varied.

4. The apparatus of claim 1 further comprising a fovea projector including an objective lens, and an eyepiece oriented such that light entering through the fovea window is detectable at the eyepiece.

5. The apparatus of claim 1 further comprising an intraocular lens in the intraocular lens holder and liquid in the basin.

6. The apparatus of claim 5 further comprising a plurality of intraocular lenses each having different optical powers, each intraocular lens successively positionable in the intraocular lens holder.

7. The apparatus of claim 5 further comprising a cornea mounted to the cornea mount.

8. The apparatus of claim 7 further comprising a plurality of corneas each having different optical powers, each cornea successively mountable to the cornea mount.

9. The apparatus of claim 1 further comprising a bifocal intraocular lens mounted to the intraocular lens holder.

10. The apparatus of claim 1 further comprising a bifocal cornea mounted to the cornea mount.

11. The apparatus of claim 10 wherein the bifocal cornea includes a portion positioned off-axis and having a power different from a remainder of the bifocal cornea.

12. The apparatus of claim 1 further comprising a moveable bellows mounted to the basin and the fovea window, wherein the fovea window is movably mounted relative to the basin.

13. The apparatus of claim 1 further comprising a moveable shaft mounted to the basin, the fovea window mounted to the shaft, and further comprising a shaft seal between the shaft and the basin.

14. The apparatus of claim 1 further comprising a control mechanism, wherein the intraocular lens holder is mounted to the control mechanism to move the intraocular lens holder relative to the basin on an x-axis, a z-axis and about an angle theta.

15. The apparatus of claim 14 further comprising a position sensor for sensing a position of the intraocular lens holder.

16. The apparatus of claim 1 wherein the basin, the cornea mount, and the intraocular lens holder are components of an eye model that is mounted on a fovea projector having an eyepiece; and further comprising a target box with a moveable target; wherein the target is in the field of view from the eyepiece of the fovea projector through the eye model.

17. The apparatus of claim 1 further comprising a camera positioned to receive the light leaving the basin at the fovea window.

18. The apparatus of claim 1 wherein the basin includes a pressurized sealed chamber.

19. The apparatus of claim 1 further comprising symbols on the fovea window.

20. A method for simulating vision comprising the steps of:

providing an eye model including a cornea, a cornea mount holding the cornea, an intraocular lens, an intraocular lens holder holding the intraocular lens, and a liquid filled basin;

positioning the intraocular lens inside the basin;

passing light from a first target through the cornea and then through the intraocular lens; and passing the light from the intraocular lens out of the basin.

21. The method of claim 20 further comprising the step of replacing the intraocular lens in the intraocular lens holder with a second intraocular lens.

22. The method of claim 20 further comprising the step of replacing the cornea with a second cornea.

23. The method of claim 20 wherein the intraocular lens projects more than one image of the first target.

24. The method of claim 20 wherein the cornea projects more than one image of the first target.

25. The method of claim 20 further comprising the step of changing the position of the intraocular lens relative to the basin.

26. The method of claim 20 further comprising the step of passing light from a second target at a different distance from the human eye model through the cornea, through the intraocular lens, and then out of the basin.

27. The method of claim 20 further comprising the steps of:

providing a fovea window in the liquid filled basin;

viewing symbols on the fovea window through the fovea window; and viewing the light from the first target through the cornea, the intraocular lens and the fovea window.

28. The method of claim 20 further comprising the step of pressurizing the liquid filled basin.

29. The method of claim 20 further comprising the step of recording an image of the light passing out of the basin with a camera.

30. The method of claim 20 wherein the cornea has about zero power.

* * * * *